(12) United States Patent  (10) Patent No.:     US 8,725,096 B2
Lint et al.                    (45) Date of Patent:         May 13, 2014

(54) CIRCUIT BOARD FOR CONTROLLING WIRELESS DENTAL HANDPIECE

(75) Inventors: Kevin Kenneth Lint, Seven Valleys, PA (US); Joseph Robert Reagan, Steelton, PA (US)

(73) Assignee: DENTSPLY International Inc., York, PA (US)

( * ) Notice: Subject to any disclaimer, the term of this patent is extended or adjusted under 35 U.S.C. 154(b) by 342 days.

(21) Appl. No.: 13/084,663

(22) Filed: Apr. 12, 2011

(65) Prior Publication Data

US 2011/0275327 A1     Nov. 10, 2011

Related U.S. Application Data

(60) Provisional application No. 61/323,142, filed on Apr. 12, 2010, provisional application No. 61/323,129, filed on Apr. 12, 2010, provisional application No. 61/323,159, filed on Apr. 12, 2010, provisional application No. 61/323,120, filed on Apr. 12, 2010.

(51) Int. Cl.
*H04B 1/18*     (2006.01)

(52) U.S. Cl.
USPC ........................................ 455/161.2; 434/263

(58) Field of Classification Search
USPC ........................................ 455/574, 95, 127.5
See application file for complete search history.

(56) References Cited

U.S. PATENT DOCUMENTS

| | | |
|---|---|---|
| 7,422,432 B2 | 9/2008 | Warner |
| 7,439,463 B2 | 10/2008 | Brenner et al. |
| D595,851 S | 7/2009 | Karten et al. |
| 2003/0232305 A1 | 12/2003 | Warner |
| 2004/0115591 A1 | 6/2004 | Warner |
| 2005/0130097 A1 | 6/2005 | Warner |
| 2005/0130098 A1 | 6/2005 | Warner |
| 2006/0024642 A1 | 2/2006 | Stadeker |
| 2006/0184092 A1 | 8/2006 | Atanasoska et al. |
| 2006/0210948 A1 | 9/2006 | Rose et al. |
| 2007/0030166 A1 | 2/2007 | Warner et al. |
| 2007/0031780 A1 | 2/2007 | Warner et al. |
| 2007/0031781 A1 | 2/2007 | Warner et al. |
| 2007/0031782 A1 | 2/2007 | Warner et al. |
| 2007/0166661 A1 | 7/2007 | Brenner et al. |
| 2007/0254261 A1 | 11/2007 | Rosenblood et al. |
| 2008/0064007 A1 | 3/2008 | Carron et al. |
| 2008/0166685 A1 | 7/2008 | Rosenblood et al. |
| 2008/0262412 A1 | 10/2008 | Atanasoska et al. |
| 2009/0081610 A1 | 3/2009 | Hayman et al. |
| 2009/0092955 A1* | 4/2009 | Hwang .......................... 434/263 |

FOREIGN PATENT DOCUMENTS

WO     2005053561 A2     6/2005

* cited by examiner

*Primary Examiner* — Tu X Nguyen
(74) *Attorney, Agent, or Firm* — Leana Levin; Douglas J. Hura; David A. Zdurne (57) ABSTRACT

A system, method, and apparatus including a printed circuit board for wireless communication between the various components and devices used in a wireless dental device. The printed circuit board includes a substrate for mounting of a plurality of electronic components. The electronic components include a programmable controller; a radio frequency transceiver; an accelerometer; a wake-up device for generating a wake-up signal to the controller; and a 2.45 GHz antenna communicatively coupled with the RF transceiver. The electronic components are in electronic communication through printed circuit traces on the substrate and configured to communicate with at least one remote wireless controller. The PCB is configured to be mounted within a housing module of the hand-held dental hand piece.

21 Claims, 5 Drawing Sheets

CIRCUIT BOARD FOR CONTROLLING WIRELESS DENTAL HANDPIECE

This application claims priority to and the benefit of U.S. Provisional Patent Application No. 61/323,142 filed Apr. 12, 2010; U.S. Provisional Patent Application No. 61/323,129 filed Apr. 12, 2010; U.S. Provisional Patent Application No. 61/323,159 filed Apr. 12, 2010; and U.S. Provisional Patent Application No. 61/323,120 filed Apr. 12, 2010 all of which are hereby incorporated by reference in their entirety.

FIELD OF THE DISCLOSURE

The present disclosure is directed to dental instruments used for cleaning and polishing teeth. More particularly, the disclosure relates to a circuit board for controlling a wireless dental hand piece.

BACKGROUND OF THE DISCLOSURE

A dental handpiece for use in cleaning and polishing teeth and other dental procedures may be adapted to receive a variety of attachments. For example, a prophylaxis angle, or prophy angle. The prophy angle (10) is attached to a dental handpiece by inserting the drive shaft into a chuck system such as a collet or other retaining means in the handpiece, for example, ISO 3964 locking system. In addition, the sleeve portion of the prophy angle may contain a slot adapted for receiving a standard positioning pin or finger on the handpiece. The extended slot permits the free end of the prophy angle to expand and prevents rotation. The chuck jaws hold the shaft in place and operatively couples the shaft to an electrical or air-driven motor inside of the handpiece. When an operator powers on the handpiece, the connected drive shaft of the prophy angle rotates and the driving gear intermeshes with the driven gear, causing the prophy angle to rotate along with an attached prophy cup.

Cordless dental handpieces for use in cleaning and polishing teeth and other dental procedures are generally configured to communicate with a selector module located proximate to the handpiece. The selector module communicates the selection of the handpiece to a foot pedal. The foot pedal may be capable of communication with more than one dental instrument, and must complete a handshake or confirmation of the received handpiece selection signal. The foot pedal then communicates control commands to the selector module, which commands are communicated to the cordless handpiece. The handpiece does not communicate directly with the foot pedal in such a configuration, because the ability of the foot pedal to control multiple instruments requires a discrete selection procedure before the foot pedal can communicate commands to the handpiece through the selector module.

Other cordless devices exist in which the cordless handpiece communicates RF signals directly with a dedicated wireless foot pedal. In such cases the foot pedal is configured to communicate exclusively with the cordless handpiece, in other words, the foot pedal cannot be used to control other dental equipment in the operatory.

What is needed is a cordless dental handpiece with capability of sending and receiving RF communications signals in a wireless communication system having a wireless foot pedal. What is also needed is an electronic circuit or circuit board for the cordless handpiece for facilitating such communication between cordless dental hygiene system components, such as the foot pedal and the various other dental operatory devices.

SUMMARY OF THE DISCLOSURE

In one aspect the disclosure includes a printed circuit board for a dental handpiece. The printed circuit boards includes a substrate for mounting of a plurality of electronic components. The electronic components include a programmable controller comprising a memory for storing software and data; a radio frequency transceiver for wireless communications with at least one remote device; an accelerometer to generate a wake-up signal to the programmable controller; and an antenna communicatively coupled with the RF transceiver. The electronic components are in electronic communication through printed circuit traces on the substrate, and communicate with at least one remote wireless controller. The printed circuit board is mountable within a housing module of the dental hand piece.

In another aspect the disclosure includes a dental handpiece having a first module detachably engageable with a dental prophylaxis angle (DPA) and a second module. The first module is an outer module extending around the second module when the first module and the second module are engaged. The second module includes a housing for a printed circuit board. The printed circuit boards includes a substrate for mounting of a plurality of electronic components. The electronic components include a programmable controller comprising a memory for storing software and data; a radio frequency transceiver for wireless communications with at least one remote device; an accelerometer to generate a wake-up signal to the programmable controller; and an antenna communicatively coupled with the RF transceiver. The electronic components are in electronic communication through printed circuit traces on the substrate, and communicate with at least one remote wireless controller.

BRIEF DESCRIPTION OF THE DRAWINGS

Wherever possible, the same reference numbers will be used throughout the drawings to represent the same parts.

DETAILED DESCRIPTION OF THE DISCLOSURE

The present disclosure now will be described more fully hereinafter with reference to the accompanying drawings, in which an exemplary embodiment of the disclosure is shown. This disclosure may, however, be embodied in many different forms and should not be construed as limited to the embodiments set forth herein.

Figure 1:
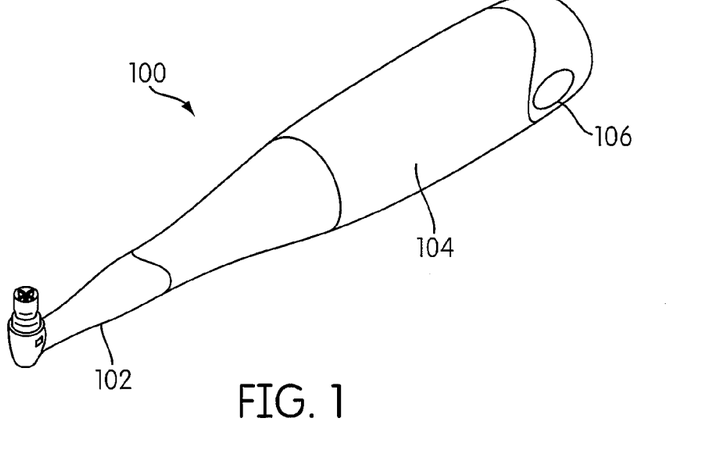
FIGS. 1-2 show a dental hand piece that may be used with the present invention.
Figure 2:
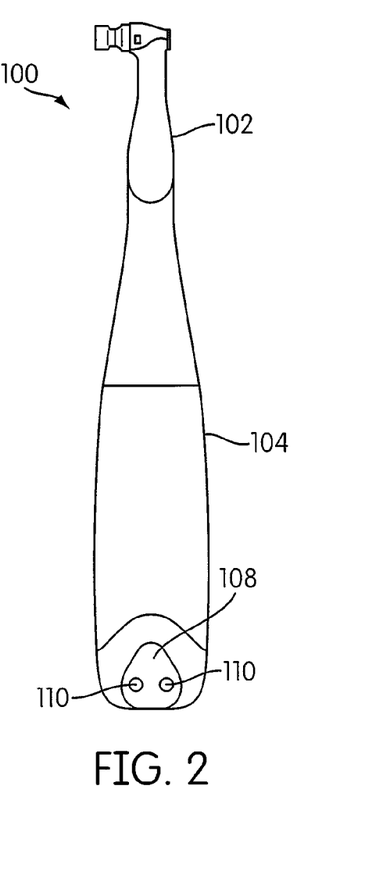

FIG. 1 shows a dental hygiene system 100. System 100 can include a dental prophylaxis angle (DPA) 102 and a dental handpiece 104. DPA 102 can be any DPA including, but not limited to, the DPA disclosed in U.S. patent application Ser. No. 12/004,155, which is hereby incorporated by reference in its entirety. Dental handpiece 104 can detachably engage DPA 102. Dental handpiece 104 can include an indicator 106 (for example, an LED display) for displaying information. Additionally or alternatively, dental handpiece 104 can include a power interface 108, or battery recharge interface.

Power interface 108 can electrically connect a battery (not shown) housed in a battery compartment (not shown) within dental handpiece 104 to a power source (not shown). Power interface 108 can include one or more contacts 110 permitting electrical communication between the power source and the battery. System 100 can be designed to have smooth transitions and/or tight tolerances between DPA 102, dental handpiece 104, indicator 106, power interface 108, and/or contacts 110.

Figure 3:
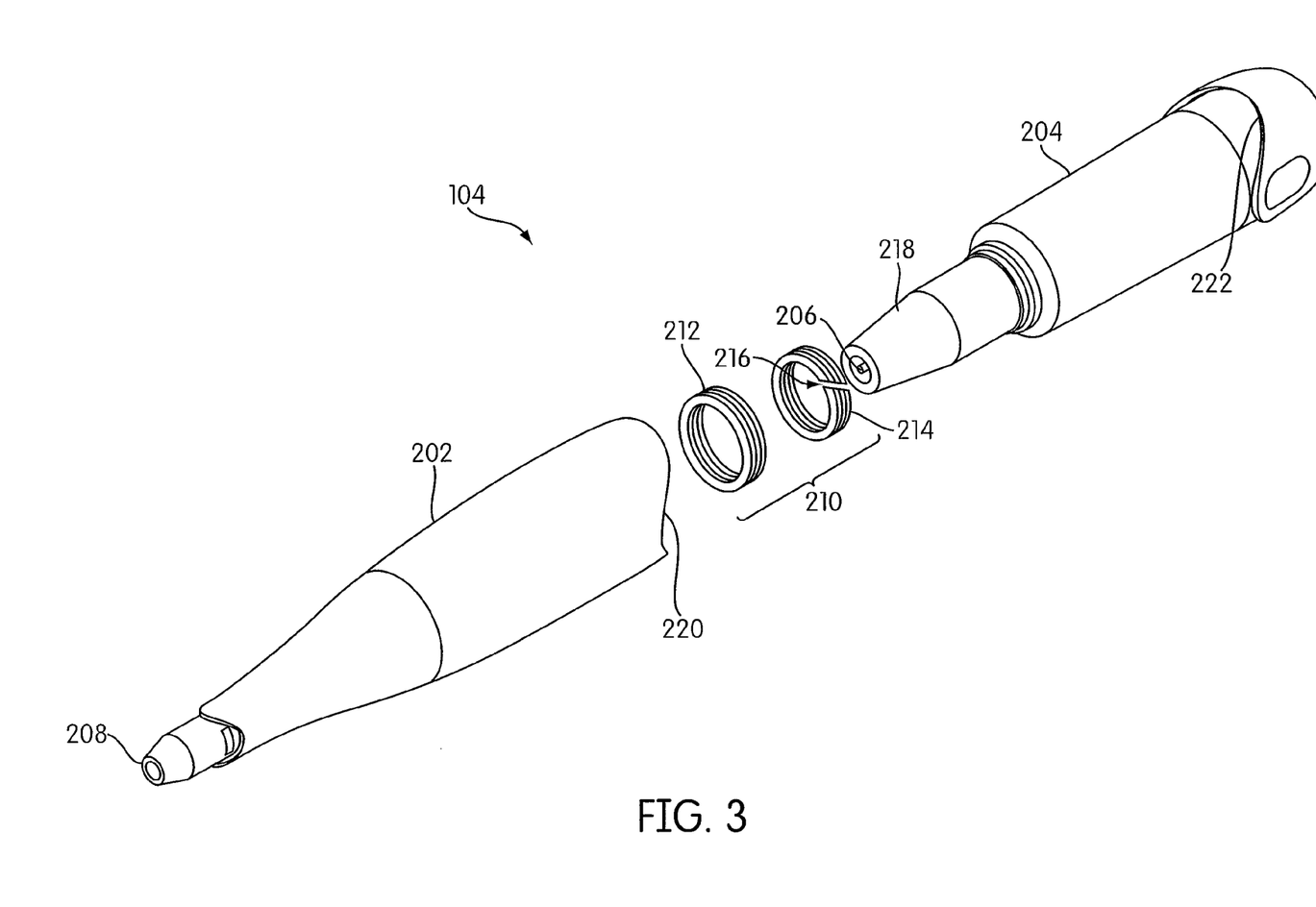
FIG. 3 shows an exploded view of the dental hand piece.

Referring to FIG. 3, dental handpiece 104 can include a first module 202 and a second module 204. First module 202 can detachably engage DPA 102 to form system. First module 202 can be an outer module configured to extend around second module 204 when engaged. First module 202 can include additional features permitting improved sterilizing and/or disinfecting. In one embodiment, first module 202 is designed to be sterilized by autoclaving materials. In another embodiment, first module 202 may include few or no rough areas thereby reducing or eliminating regions for depositing undesirable substances.

Figure 4:
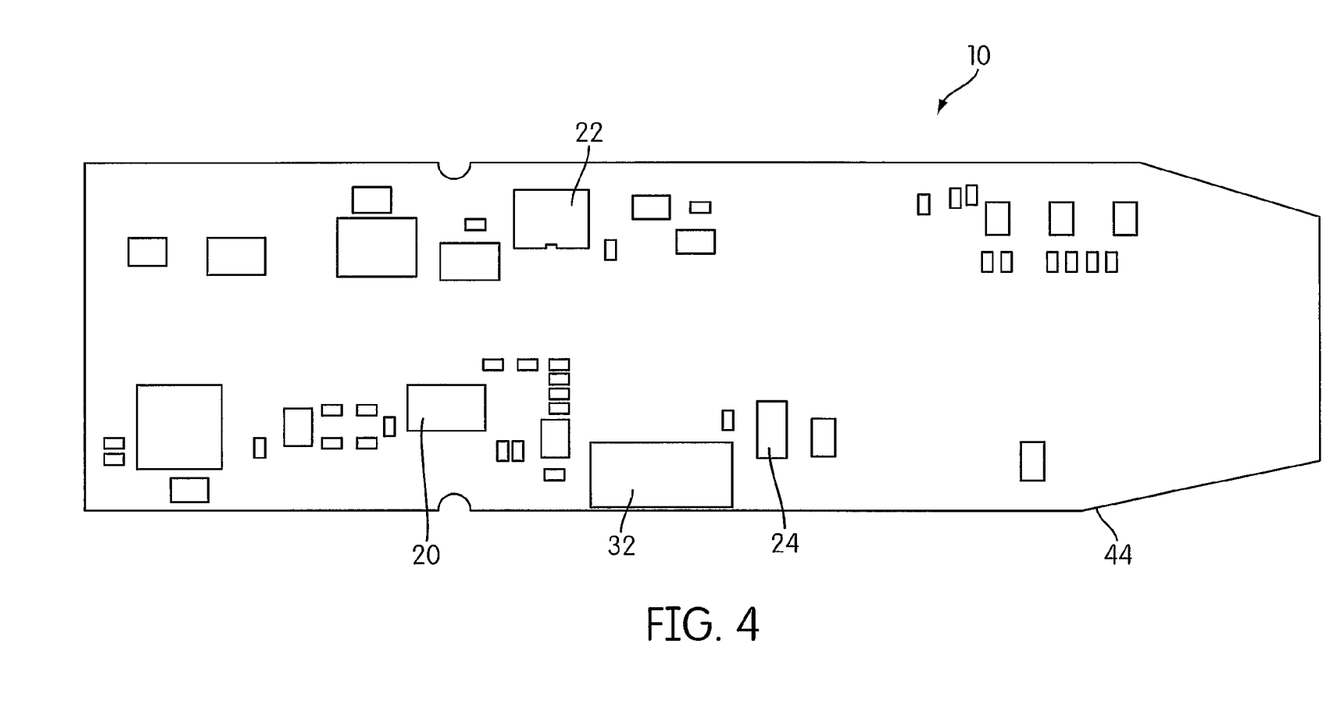
FIG. 4 shows a plan view of one side of a printed circuit board for controlling the dental hand piece.

FIG. 4 shows a first side of a handpiece controller printed circuit board (PCB) 10. PCB 10 is housed within second module 204. PCB 10 includes a battery coulomb counter 20 which preferably may include non-volatile memory, e.g., electrically-erasable programmable read-only memory integrated circuit (EEPROM), a linear single cell lithium ion charger 22, a low noise regulator 24, and a tilt switch 32. Additional circuit elements shown on PCB 10 but not described herein include connector blocks for connecting external components to PCB 10, various diodes, capacitors, resistors inductors, test points, voltage suppressors and other circuit elements, details of which are known to those skilled in the art and which are not required for an understanding of the disclosure. By external component, what is meant is an electrical component on dental handpiece 100 that is connected by wire conductors to PCB 10.

Figure 5:
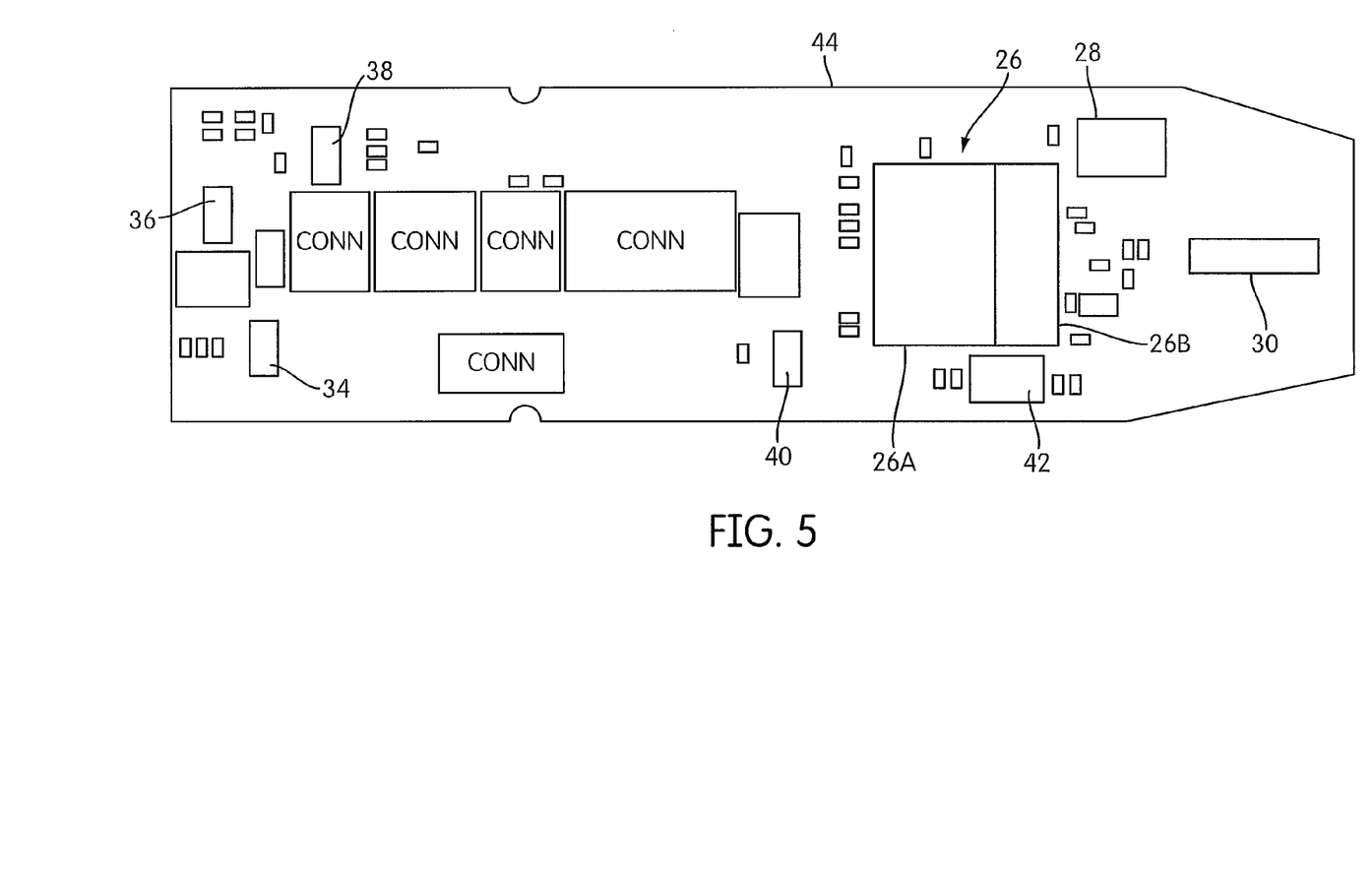
FIG. 5 shows a plan view of the opposite side of the printed circuit board of FIG. 4.

Referring next to FIG. 5, an opposite side of PCB 10 is shown, including integrated circuit 26 with a microcontroller 26A and a radio frequency (RF) transceiver 26B, an antenna 30. an accelerometer 28, boost converter 34, current monitor 36, buffered power half-bridge 38 for driving a motor, serial EEPROM 40, and a 16 megahertz (MHz) crystal 42.

The circuit components identified above with respect to FIGS. 4 & 5 are in electronic communication through printed circuit traces within the substrate 44. Non volatile memory portion of microcontroller 26A may in various alternate embodiments be something other than EEPROM, e.g., flash memory, other forms of read-only memory that is capable of retaining stored information when power is lost. In at least one exemplary embodiment RF transceiver may be a 2.4 GHz RF transceiver, and the antenna configured for 2.45 GHz antenna transmission. 2.45 GHz is the nominal or center frequency. In a preferred embodiment the actual signal transmissions of the 2.4 GHz RF transceiver may be in a range from 2.405 to 2.480 GHz. Broadly stated, RF transceiver and antenna may be configured for any RF frequency provided that they are compatibly tuned for the selected frequency. The voltage regulator may be preferably configured for 2.5 volts, although a voltage regulator for any suitable operating voltage may be used.

Microcontroller 26A provides logic control for all of the components and wireless communications between hand piece 100 and a remote foot pedal controller (not shown). For example, communications and logic control may include software, hardware and combinations thereof for synchronizing hand piece 100 with at least one wireless foot pedal controller, for selectively pairing with the foot pedal and controlling hand piece 100. Any integrated circuit known in the art is suitable for use herein regardless of amount of flash memory and RAM.

Antenna 30 is connected to transceiver 26B to provide RF input signals to transceiver 26B. Antenna 30 is configured for communications in the appropriate standard, e.g., ZigBee, Bluetooth, IEEE 802.11 or telemetry.

Transceiver 26B may be, for example in a preferred embodiment, a ZigBee™ compliant platform 2.4 GHz low power transceiver plus microcontroller or other transceiver capable of compliance with IEEE® 802.15.4 standard. Transceiver 26B may be an RF transceiver which is an 802.15.4 standard compliant radio that operates in the 2.4 GHz ISM frequency band. Transceiver 26B may include a low noise amplifier, for example, 1 mW nominal output power, with internal voltage controlled oscillator (VCO), integrated transmit/receive switch, on-board power supply regulation, and full spread-spectrum encoding and decoding. Transceiver 26B may preferably include a microcontroller unit, for example, HCS08 Version A.

Transceiver 26B provides an electrical interface between an asynchronous communication controller and the serial-port connector for handling data communications. Transceiver 26B may be a serial interface, e.g., RS-232, USB, I$^2$C, SPI and comparable serial interfaces.

Tilt switch 32 acts like a position sensitive switch which is normally closed when below horizontal and normally open when above horizontal. When at rest it normally settles in a close state. When in motion, it will produce continuous on/off contact closures. It is sensitive to both tilt, or static acceleration, and vibration or dynamic acceleration.

In another embodiment, switch 32 may be normally open when vertical, and normally closed below the switch angle. When at rest in a vertical position, the sensor will settle in an open state. When tipped down from vertical to the "switch angle" it will produce continuous on/off contact closures while in motion. When at rest below the switch angle, switch 32 will settle in a normally closed position. Switch 32 can be used to produce a series of CMOS or TTL level logic level or pulse train using a single resistor to limit current. The signal level can be read directly by a digital input and used to interrupt or wake up a microcontroller, or the signals can be counted to estimate the amount and duration of activity. Switch 32 may be non-sensitive to lateral movement when vertical. Alternately, switch 32 may be sensitive to lateral movement when vertical. Switch 32 may be, e.g., a SQ-SEN 390, 600 or 700 series sensor manufactured by Signal Quest, Inc. of Lebanon, N.H.

In the hand piece 100, tilt switch 32 may be used to provide signals to microcontroller 26A to indicate the level and timing of activity so that, when communicated via antenna 30 to the foot pedal controller device, the foot pedal control logic may algorithmically determine which device of a plurality of devices is selected.

Voltage regulator 24 may be, e.g., LP2981—Micropower 100 mA Ultra Low-Dropout Regulator manufactured by National Semiconductor Corp. of Santa Clara, Calif. In one embodiment voltage regulator may be a 100 mA, fixed output voltage regulator for battery-powered applications. Dropout voltage may be about 200 mV at 100 mA load, and 7 mV at 1 mA load. Ground pin current is typically in a range of about 600 µA at 100 mA load, and 80 µA at 1 mA load. For sleep mode regulator 24 may draw less than 1 µA quiescent current when ON/OFF pin is pulled low.

Accelerometer 28 detects when hand piece 100 is moved. In one embodiment accelerometer 28 is an integrated-circuit accelerometer. Accelerometer 28 may include a capacitive sensing cell (g-cell) and a signal conditioning ASIC. The g-cell is a mechanical structure formed from semiconductor materials. The ASIC uses switched capacitor techniques to measure the g-cell capacitors and extract the acceleration data from the difference between the two capacitors. The ASIC also signal conditions and filters the signal, providing an output voltage that is ratiometric and proportional to acceleration. Ratiometric means that the output offset voltage and sensitivity is scaled substantially linearly with applied supply voltage. As supply voltage is increased, the sensitivity and offset increase linearly; as supply voltage decreases, offset and sensitivity decrease linearly. In a preferred embodiment the accelerometer 28 may provide a sleep mode feature to conserve battery power during extended periods when hand piece 100 is not in use. When sleep mode is active, accelerometer 28 outputs are turned off to reduce operating current. When a wake-up signal is received by accelerometer 28, it resumes a normal mode of operation.

Another main function of the accelerometer is to identify the activity level of the associated device. The activity level—generally the highest activity level or the most recent activity level, or a combination thereof—determines which handpiece gets the communication taken from the foot pedal if two or more handpieces are active. The accelerometer can be used in place of the tilt switch.

In another exemplary embodiment, accelerometer 28 may also include a self test feature to permit verification of the mechanical and electrical integrity of accelerometer 28. In another embodiment, accelerometer 28 may include plural sensitivity settings—referred to as g-select settings—which allows for the selection between two or more sensitivities. Depending on the a logic input signal, accelerometer 28 internal gain may be changed to allow it to function, for example, with a 3g or 11g sensitivity. The g-Select option can be omitted if hand piece 100 requires only a single, e.g., 3g, sensitivity.

Battery voltage declines as stored power is drained. Switched DC to DC converters offer a method to increase voltage from a partially lowered battery voltage thereby saving space instead of using multiple batteries to accomplish the same thing. Boost converter 34 is a DC to DC converter which uses the varying input battery voltages (4.2 volts to 2.5 volts) and steps the voltage up to a higher constant voltage source for the motor drive circuits. The higher voltages allow motor operation at higher speeds and in turn also allow higher torque compensation. In DC to DC boost converter 34 operates in conjunction with three other components. These components include an inductor or magnetic storage device, a diode, and a capacitor as a charge storage device. In the charge phase the boost converter 34 connects one side of the inductor to ground while the other side of the inductor remains connected to the battery. This connection configuration induces a current flow through the inductor. Once the current flow has started boost converter 34 changes the circuit to a discharge state by removing the ground connection on one side of the inductor. In this phase the inductor now becomes a current source to charge the capacitor through the diode in the circuit. The voltage on the capacitor increases for a time set by boost converter 34 at which time the converter repeats the cycle. The output voltage is controlled by the boost converter through feedback lines which monitor the output voltage. Boost converter 34 changes the pulse widths which control the charge and recharge phases of the control cycle to give a constant and higher voltage on the output as compared to the supplied input voltage from the battery.

In at least one exemplary embodiment, current monitor 36 may be a fast current gauge IC with ultra low loss sense element and pulse-width modulated (PWM) output, Model No. LM3814/LM3815, manufactured by National Semiconductor Corp. Current monitor 36 provide current measurement with very low insertion loss, e.g., about 0.0040. In one embodiment the current and the direction of the current that is being monitored can be determined by measuring the pulse widths of the PWM signal and digitally averaging the resultant signal in a microcontroller. In another embodiment the current may be determined by filtering the PWM signal through a low pass filter to generate an equivalent analog voltage signal representative of the current being monitored. An analog-to-digital converter may be used to precisely measure the analog voltage signal representing the current and to provide a current averaging function. E.g., current may be averaged over 6 msec time periods to provide immunity to current spikes. Current monitor 36 may include a pulse-width modulated (PWM) output which indicates the current magnitude and direction. Current monitor 36 monitors motor current.

Buffered power half-bridge 38, may be, e.g., AAT4900 FastSwitch manufactured by AnalogicTech of Santa Clara, Calif. Half-bridge 38 may be a buffered power half-bridge consisting of low resistance power MOSFETs with integrated control logic which operates with inputs ranging from 2.0V to 5.5V and preferably with control circuitry to protect from shoot-through current. Half-bridge 38 is preferably capable of very fast switching times for use in high frequency DC/DC converters or pulse width modulated motor drives. In shutdown mode, the supply current draw of half-bridge 38 may decreases to less than 1 µA. Half-bridge 38 drives a DC motor providing mechanical power from the hand piece 100.

Serial EEPROM 40 provides RS-232 memory and control memory capacity, e.g., 1K EEPROM. EEPROM 40 may be, e.g., a Microchip Technology, Inc., Model No. 24AA01t-I/OT. EEPROM 40 provides long term storage of variables in the program such as address and communication channel information. In an alternative embodiment, the memory function can also be performed in flash memory.

Crystal 42 is used to provide a clock signal to microcontroller 26A. Crystal 42 may be, e.g., a 16 megahertz (MHz) TSX-4025—MHz Range Crystal Unit with a nominal frequency range of about 12 MHz to 32 MHz.

Figure 6:
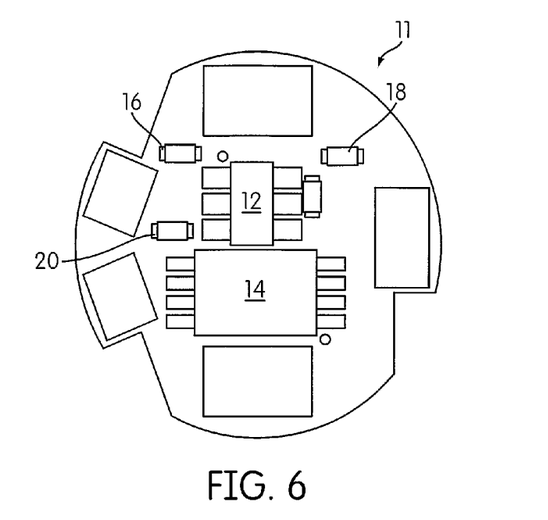
FIG. 6 shows a battery protection circuit board that can be mounted on the end of an AA battery.

A battery (not shown) may be housed within second module 204. The battery may be a rechargeable lithium ion battery, lithium polymer battery, or any suitable rechargeable battery. Charger 22 is located on PCB 10 (FIG. 4). Charger 22 may be a linear single cell lithium ion charger or any charger suitable for use with the battery housed in module 204. The battery includes a battery protection module. The battery protection circuit includes a MOSFET N-channel integrated circuit, a thermistor, resistors and capacitors. Additional electronic components not described herein may be included on the PCB 10. For example, charger 22 may be in electrical communication with battery protection circuit board 11. Battery circuit board 11 may include a Seiko battery protect IC for a lithium ion 4.275 volt single cell battery (not shown), MOSFET an N-channel dual volt, 3.3 thin shrink small outline package (TSSOP) device, a first resistor may be, e.g., a 470 ohm, 1/16 watt resistor for surface mounting, a second resistor may be, e.g., a 2.20 kilo-ohm, 1/16 watt resistor for surface mounting, a thermistor may be a 10 kilo-ohm negative temperature coefficient thermistor, and a capacitor may be a ceramic, 0.1 or 1 micro-farad capacitor. It will be understood that any of the electrical, electronic and physical parameters of the electronic components on charger 22 described herein are exemplary and may be modified or varied to suit other applications or conditions.

In further embodiments battery coulomb counter 20 may be located on PCB 10 (FIG. 4). Battery coulomb counter 20 may be a single cell lithium ion battery coulomb counter system and may be in direct communication with the rechargeable battery (not shown), the charger 22 and the microcontroller 26A. The battery coulomb counter 20 can provide critical information such as state-of-charge information, battery temperature information, capacity monitoring information of the connected battery, and can turn the entire system off if the amount of charge in the system reaches a critically low set point. For example, as the amount of charge or coulombs remaining on the battery are depleted due to use of the system, the microcontroller 26A may query the battery coulomb counter 20 as to the state of charge, charge capacity, battery temperature and make system operational decisions based on the remaining charge state, temperature or capacity of the connected battery.

Figure 7:
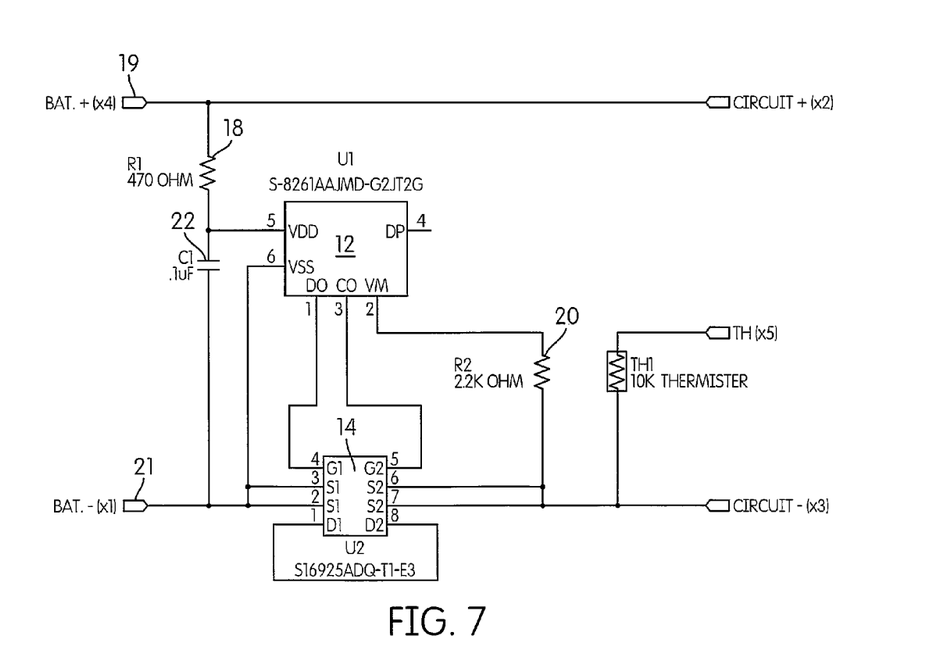

FIGS. 6 and 7 show an exemplary battery protection circuit board and battery protection schematic, respectively. The battery protection circuit board 11 is mountable on the axial end of the lithium battery. The battery protection circuit board 11 is configured for protection of a single-cell lithium ion/lithium polymer battery pack (not shown), to prevent overcharge, over discharge and overcurrent. In one embodiment, the battery protection circuit board 11 monitors the voltage of a lithium battery connected between VDD pin and VSS pin and the voltage difference between VM pin and VSS pin to control over charging and over discharging of the lithium battery. Resistor 18 (R1) is connected between a battery positive terminal 19 and a positive voltage input of protection I.C. 12 Seiko I.C. and capacitor 22 (C1) on the opposite terminal. Resistor 20 (R2) is connected between voltage detection pin VM and the negative battery terminal 21. Thermistor 16 provides a sensor to indicate the temperature of the battery pack. Protection I.C. 12 outputs DO and CO provide gate controls signals to MOSFET IC 14 for discharge and charge, respectively.

When the battery voltage is in the range from the over discharge detection voltage (VDL) to the overcharge detection voltage (VCU), and the VM pin voltage is in the range from the charger detection voltage (VCHA) to the overcurrent 1 detection voltage (VIOV1), the IC turns both the charging and discharging control FETs on. This condition is called the normal condition, and in this condition charging and discharging can be carried out freely.

When a battery in the normal status is in the status where the voltage of the VM pin is equal to or higher than the overcurrent detection voltage because the discharge current is higher than the specified value and the status lasts for the overcurrent detection delay time, the discharge control FET is turned off and discharging is stopped. This status is called the overcurrent status. In the overcurrent status, the VM and VSS pins are shorted by the resistor between VM and VSS (RVMS) in the IC. However, the voltage of the VM pin is at the VDD potential due to the load as long as the load is connected. When the load is disconnected, the VM pin returns to the VSS potential. This IC detects the status when the impedance increases and is equal to the impedance that enables automatic restoration and the voltage at the VM pin returns to overcurrent detection voltage 1 or lower and the overcurrent status is restored to the normal status.

When the battery voltage exceeds the overcharge detection voltage during charging under the normal condition and the detection continues for the overcharge detection delay time or longer, the battery protection circuit turns the charging control FET off to stop charging. The overcharge condition is released when the battery voltage falls below the overcharge release voltage-overcharge detection hysteresis voltage, IC 12 turns the charging control FET on and turns to the normal condition, or when a load is connected and discharging starts, Protection I.C. 12 turns the charging control FET on and returns to the normal condition. After the load is connected and discharging starts, the discharging current flows through the parasitic diode in the charging control FET. At this moment the VM pin potential becomes Vf, the voltage for the parasitic diode, higher than VSS level. When the battery voltage goes under the overcharge detection voltage and provided that the VM pin voltage is higher than the overcurrent 1 detection voltage, IC 12 releases the overcharge condition.

While only certain features and embodiments of the invention have been shown and described, many modifications and changes may occur to those skilled in the art (for example, variations in sizes, dimensions, structures, shapes and proportions of the various elements, values of parameters (for example, temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A printed circuit board for a dental handpiece comprising:
   a substrate for mounting of a plurality of electronic components, the electronic components comprising:
   a programmable controller comprising a memory for storing software and data;
   a radio frequency transceiver for wireless communications with at least one remote device;
   an accelerometer to generate a wake-up signal to the programmable controller; and
   an antenna communicatively coupled with the RF transceiver;
   the electronic components in electronic communication through printed circuit traces on the substrate and configured to communicate with at least one remote wireless controller;
   the printed circuit board mountable within a housing module of the dental hand piece.

2. The printed circuit board of claim 1, wherein the accelerometer detects a movement of the dental handpiece.

3. The printed circuit board of claim 1, wherein the accelerometer determines an activity level of the dental handpiece, wherein the activity level is transmitted to the programmable controller to determine if the dental handpiece comprises a highest activity level or a most recent activity level, or a combination of the highest and most recent activity level, among a plurality of addressable devices.

4. The printed circuit board of claim 1, wherein the accelerometer comprises an integrated-circuit accelerometer.

5. The printed circuit board of claim 1, wherein the accelerometer comprises a capacitive sensing cell and a signal conditioning application-specific integrated circuit, wherein the application-specific integrated circuit:
   measures the capacitive sensing cell and extract acceleration data from a difference between two capacitors; and
   provides an output voltage signal that is proportional to acceleration and scaled substantially linearly with an applied supply voltage.

6. The printed circuit board of claim 1, wherein the accelerometer is capable of a sleep mode such that operating currents are reduced, and upon receipt of a wake-up signal by the accelerometer, normal modes of operation are resumed.

7. The printed circuit board of claim 1, wherein the accelerometer further comprises a self-test feature configured to verify a mechanical and an electrical integrity of the accelerometer.

8. The printed circuit board of claim 1, further comprising a battery charger and a battery coulomb counter; the battery charger and battery coulomb counter configured to monitor a charge of a battery for powering the printed circuit board.

9. The printed circuit board of claim 1, further comprising a boost converter to receive a voltage from an input battery and increase the voltage to a constant voltage source for a motor drive.

10. The printed circuit board of claim 9, wherein the input battery voltage varies between about 4.2 volts to 2.5 volts.

11. The printed circuit board of claim 1, further comprising a current monitor to measure a motor current and a direction of current based on a pulse width of a PWM signal.

12. The printed circuit board of claim 1, further comprising a current monitor to measure a motor current based on filtering a PWM signal through a low pass filter to generate an equivalent analog voltage signal representative of the motor current being monitored.

13. The printed circuit board of claim 1, further comprising a current monitor comprising a fast current gauge integrated circuit with ultra low loss sense element and pulse-width modulated output.

14. The printed circuit board of claim 1, further comprising an analog-to-digital converter to measure an analog voltage signal representing a motor current, and average the motor current to provide immunity to current spikes.

15. The printed circuit board of claim 1, further comprising an electrically erasable programmable read only memory (EEPROM) comprising capacity for long term storage of variables for use in a computer program.

16. The printed circuit board of claim 1, further comprising a crystal to provide a clock signal to the programmable controller.

17. The printed circuit board of claim 1, wherein the crystal comprises a 16 megahertz (MHz) crystal with a nominal frequency range of about 12 MHz to 32 MHz.

18. The printed circuit board of claim 1, wherein the housing module further comprises a rechargeable battery mounted therein; and a battery charger located on the printed circuit board.

19. The printed circuit board of claim 1, further comprising a buffered power half-bridge comprising low resistance power MOSFETs with integrated control logic, wherein the half-bridge operates over an input range between about 2.0 volts to about 5.5 volts, and drives a DC motor that powers the dental handpiece.

20. The printed circuit board of claim 1, further comprising a battery protection circuit board mountable on the axial end of a battery, wherein the battery protection circuit board monitors the voltage of the battery connected and controls charging and discharging of the battery.

21. A dental handpiece comprising:
   a first module detachably engageable with a dental prophylaxis angle (DPA) and a second module, wherein the first module is an outer module configured to extend around the second module when the first module and the second module are engaged;
   the second module comprising a housing for a printed circuit board;
   the printed circuit board comprising:
      a substrate for mounting of a plurality of electronic components, the electronic components comprising:
         a programmable controller comprising a memory for storing software and data;
         a radio frequency transceiver for wireless communications with at least one remote device;
         an accelerometer to generate a wake-up signal to the programmable controller; and
         an antenna communicatively coupled with the RF transceiver; and
   the electronic components in electronic communication through printed circuit traces on the substrate and configured to communicate with at least one remote wireless controller.

* * * * *